United States Patent [19]

Wadwha

[11] Patent Number: 4,893,620

[45] Date of Patent: Jan. 16, 1990

[54] MULTIPURPOSE NASAL AIRWAY

[76] Inventor: Rajindar K. Wadwha, 2482 Mt. Royal Rd., Pittsburgh, Pa. 15217

[21] Appl. No.: 157,946

[22] Filed: Feb. 18, 1988

Related U.S. Application Data

[63] Continuation-in-part of Ser. No. 716,589, Mar. 27, 1985, abandoned.

[51] Int. Cl.⁴ .................. A61M 25/00; A61M 15/06; A61M 15/08; A61M 17/32
[52] U.S. Cl. ........................ 128/202.13; 128/207.18; 606/185
[58] Field of Search ........... 128/207.18, 305.3, 200.26, 128/305, 202.13, 207.14, 200, 224; 30/151; 401/195

[56] References Cited

U.S. PATENT DOCUMENTS

| | | | |
|---|---|---|---|
| 973,427 | 10/1910 | Hayes | 128/203.24 |
| 1,306,720 | 9/1921 | Powers | 128/305 |
| 1,444,155 | 2/1963 | Jorgenson | 30/151 |
| 1,611,171 | 12/1962 | Easton | 401/195 |
| 3,021,836 | 2/1962 | Marsden | 128/29 |
| 3,068,590 | 12/1962 | Padellford | 35/17 |
| 3,297,027 | 1/1967 | Rusch | 128/145.5 |
| 3,307,551 | 3/1967 | Violet, Jr. | 128/305.3 |
| 3,395,711 | 8/1968 | Plazak, Jr. | 128/200.26 |
| 3,508,543 | 4/1970 | Aulicono | 128/207.18 |
| 3,700,106 | 12/1974 | Leopoldi | 128/305 |
| 3,714,945 | 2/1973 | Stanley | 128/214.4 |
| 3,861,087 | 1/1975 | Martin | 51/205 R |
| 3,964,488 | 6/1976 | Ring et al. | 128/351 |
| 3,972,321 | 8/1976 | Proctor | 128/207.18 |
| 4,306,550 | 11/1981 | Gandi et al. | 128/207.18 |
| 4,411,653 | 10/1983 | Rizi | 604/157 |
| 4,440,161 | 4/1984 | Wadnwa | 128/305.3 |
| 4,440,161 | 4/1984 | Wadhwa | 128/202.13 |
| 4,556,059 | 12/1985 | Adamson, Jr. | 128/305.3 |

OTHER PUBLICATIONS

Safar et al., "Cricothyroid Membrane Puncture with Special Cannula", *Anesthesiology*, vol. 28, No. 5, Sep.-Oct. 1967.

*Primary Examiner*—Max Hindenburg
*Assistant Examiner*—K. M. Reiche
*Attorney, Agent, or Firm*—Arnold B. Silverman

[57] ABSTRACT

A nasal airway in a preferred embodiment includes a tubular housing and an airway tube which in the storage position is received at least partially within the tubular housing and in a second position projects outwardly therefrom. The airway tube may have one or more auxiliary openings disposed between the ends thereof. A first closure may close the end of the tubular housing to which the airway tube may be secured and a second closure may close the other end. A blade or the like for performing a tracheostomy may be associated with the second closure. A tracheostomy tube and associated cannula are provided. The multipurpose nasal airway may also be provided with writing equipment such as a reservoir of ink and associated discharge point or a flashlight or other independently useful article.

21 Claims, 2 Drawing Sheets

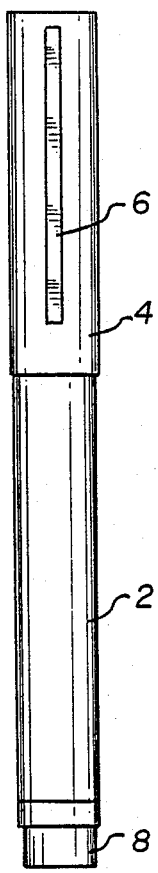
FIG. 1
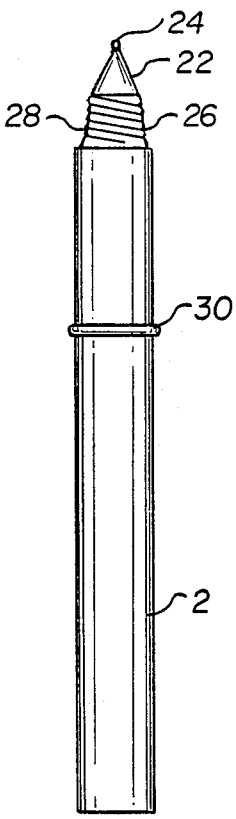
FIG. 5
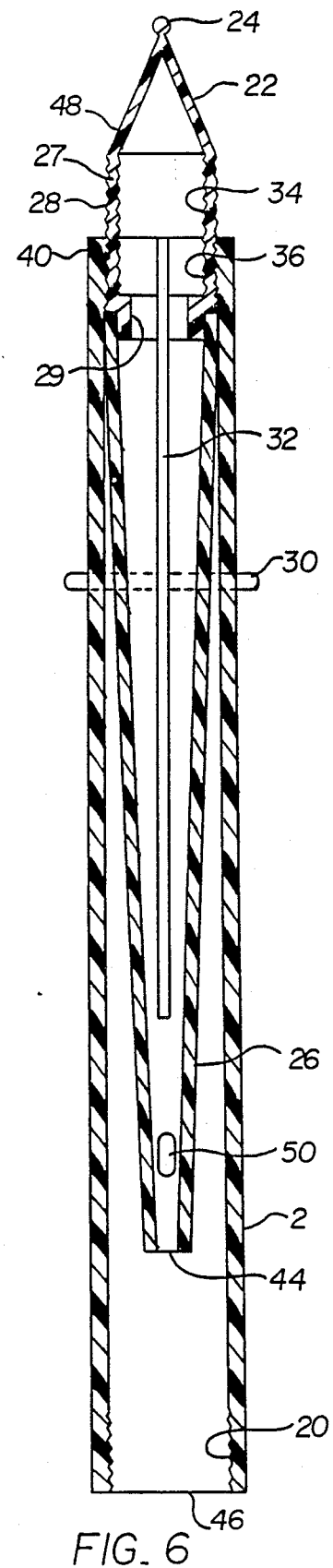
FIG. 6
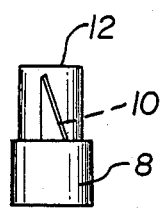
FIG. 2
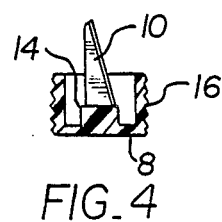
FIG. 4
FIG. 3
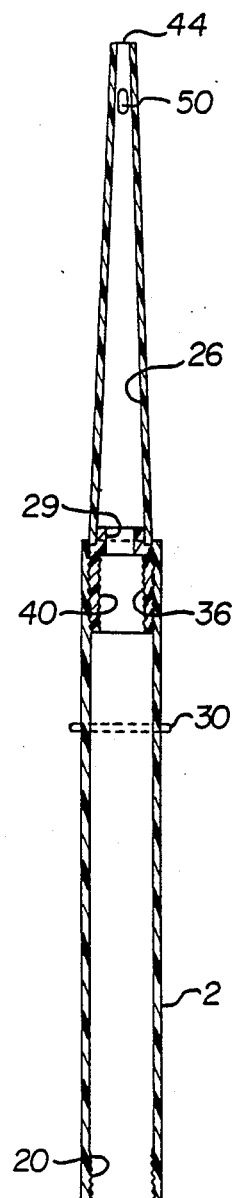
FIG. 7

MULTIPURPOSE NASAL AIRWAY

CROSS-REFERENCE TO RELATED APPLICATION

This Application is a continuation-in-part of application Ser. No. 06/716,589, filed Mar. 27, 1985, now abandoned.

BACKGROUND OF THE INVENTION

1. Field of the Invention

This invention relates generally to nasal airways and, more specifically, to such airways which are of relatively small size and are adapted to serve an independently useful purpose as well as providing means for performing an emergency tracheostomy.

2. Description of the Prior Art

It has been known during surgical procedures for anesthesiologists to place an airway into the mouth of a patient. The airway, which generally consists of a curved, plastic tube serves to keep the patient's mouth open and permits ready insertion of tubes for administering anesthesia, withdrawing mucous by suction, as well as other purposes. It is also known to employ airways which are inserted into a patient's mouth in order to initiate emergency resuscitation procedures. U.S. Pat. Nos. 3,021,836 and 3,297,027 show two examples of tubes which are introduced into a patient's mouth for resuscitation purposes. U.S. Pat. No. 3,068,590 discloses a resuscitation training device.

It has been known to provide blades in pen-like housings. See U.S. Pat. Nos. 1,444,155 and 1,611,171. It has also been known to combine a pencil holder and inhaler. See U.S. Pat. No. 973,427.

It has been known to provide surgical blades and tubes in multipiece housings. See U.S. Pat. Nos. 3,307,551 and 3,706,106. U.S. Pat. No. 1,390,720 discloses a surgical knife and case.

U.S. Pat. No. 3,508,543 discloses a resuscitation tube adapted to be introduced into the patient's mouth and having auxiliary tubes adapted to be introduced into the patient's nostrils.

In respect of most medical emergencies where resuscitation is needed, time is of the essence and, with the exception of hospitals and certain clinics and doctor's offices, in general, airways will not be readily available at the site of the emergency need. As a result of the size, cost and single-purpose nature of known airways, there remains a very real and substantial need for an airway of such design and construction as to be effective in use and to be likely to be available more readily at the scene of an emergency.

SUMMARY OF THE INVENTION

The present invention has met the above-described need by providing a multipurpose airway which is, as a result of its size and multiple uses, more likely to be carried about by physicians and other medically or paramedically trained individuals thereby enhancing the likelihood that the airway will be available where needed when needed.

The present invention is an improvement over the invention disclosed in Wadhwa U.S. Pat. No. 4,440,161, the disclosure of which is expressly incorporated herein by reference.

In the present invention, a nasal airway includes a tubular housing having an associated airway tube which may be stored in a first position and secured for use in a second position. In addition, the article may function as a writing implement, flashlight or other useful purpose and may provide means for performing an emergency tracheostomy. As the nasal airway of the present invention is preferably relatively small, such as the size of a conventional fountain or ballpoint pen, for example, and it is adapted, in one embodiment, to function as a writing implement, this additional function enhances the likelihood that an individual will carry the instrument on his or her person.

It is an object of the present invention to provide a nasal airway which is compact, economical to manufacture and easy to use.

It is a further object of the present invention to provide such a nasal airway which has means permitting it to function as a writing implement or other useful article.

It is another object of the present invention to provide such a nasal airway which has means for performing an emergency tracheostomy and includes tracheostomy tube means and an associated catheter.

It is a further object of this invention to provide airway means which will permit the one rendering medical assistance to avoid concern about the medical background of the one needing help and to avoid the need for skin, mucous membrane or mouth to mouth contact.

It is yet another object of the present invention to increase the likelihood that emergency resuscitation procedures may be undertaken effectively at the scene of an emergency in prompt fashion.

These and other objects of the invention will be more fully understood from the description of the invention on reference to the illustrations appended hereto.

BRIEF DESCRIPTION OF THE DRAWINGS

FIG. 1 is a front elevational view of a form of nasal airway assembly of the present invention.

FIG. 2 is a front elevational view of a portion of the airway of FIG. 1 which is adapted to function as a tracheostomy blade.

FIG. 3 is a top plan view of the tracheostomy blade of FIG. 2 with the blade protective covering not illustrated.

FIG. 4 is a cross-sectional illustration of the blade assembly taken through 4—4 of FIG. 3.

FIG. 5 is a front-elevational view of the nasal airway of FIG. 1 with the closure portions removed.

FIG. 6 is a cross-sectional illustration of a form of nasal airway of the present invention showing the airway tube in storage position.

FIG. 7 is a cross-sectional illustration of a form of nasal airway of the present invention showing the airway tube in usable position.

DESCRIPTION OF THE PREFERRED EMBODIMENTS

Figure 8:
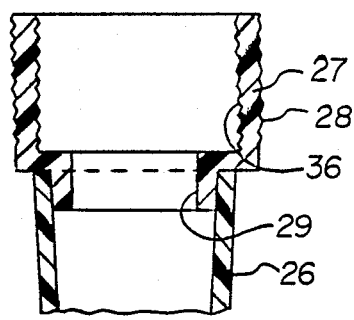
FIG. 8 is a cross-sectional illustration of a portion of a nasal airway of the present invention.
Figure 10:
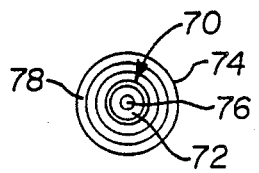
FIG. 10 is an elevational view showing a tracheostomy tube of the present invention.
Figure 9:
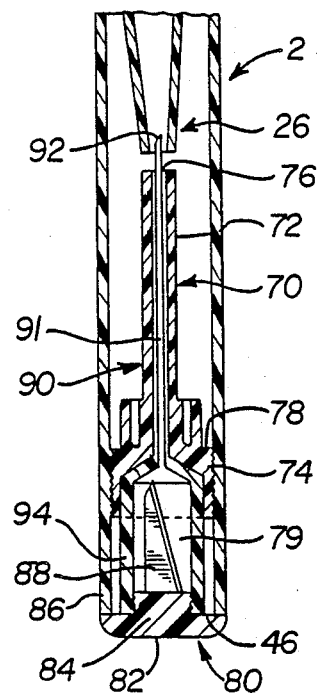
FIG. 9 illustrates a partial cross-sectional illustration of a portion of a nasal airway of the present invention showing the assembly.
Figure 11:
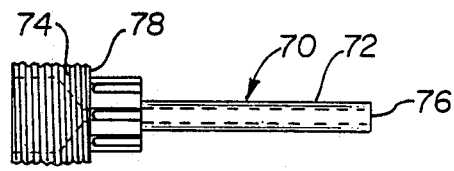
FIG. 11 is a front elevational view of the tracheostomy tube of FIG. 10.
Figure 12:
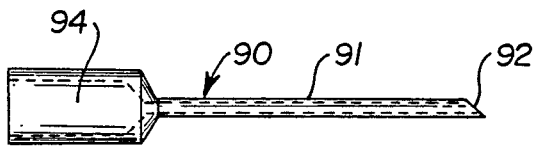
FIG. 12 is a front elevational view of the cannula employed in the assembly of FIG. 9.
Figure 13:
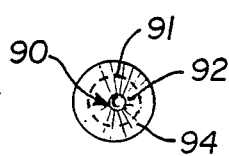
FIG. 13 is a right side elevational view of the cannula of FIG. 12.

As used herein, in the absence of an express indication to the contrary at a particular location, the term "patient" shall refer to members of the animal kingdom, including human beings.

Referring now in greater detail to FIG. 1, there is shown an embodiment of the miniaturized nasal airway of the present invention which may conveniently have the dimensions of a commercially available fountain or ballpoint pen. It may, for example, have a length of about 4 to 6 inches and a width of about ½ to ⅜ inch. In the form shown, the nasal airway has a tubular housing 2 which has a closure 4 provided with a clip 6 so as to secure the same to a pocket and a lower closure 8.

Referring now more specifically to FIGS. 2 through 4, the tracheostomy blade feature of the present invention will be considered in greater detail. In the event that the apparatus of the present invention were needed to be employed to perform a tracheostomy on an emergency basis, closure 8, which is preferably threadedly or snap-fit secured to tubular housing 2, would be removed. As removed, it would assume the appearance shown in FIG. 2 wherein the closure 8 may serve as the handle portion for permitting use of the projecting blade member 10. The blade member 10 may advantageously be composed of stainless steel, plastic or other noncorrosive material. In the form shown in FIG. 2, a protective material 12 such as a plastic film is positioned over the blade 10 in order to maintain blade cleanliness, avoid inadvertent cutting by the blade and, in the event of use of a corrosion-susceptible material in the blade, to resist corrosion. The film or cover 12 would be stripped from the blade member 10 thereby permitting use of the same.

Referring to FIGS. 3 and 4, it is noted that in order to reinforce the connection between the blade 10 and the closure 8, a pedestal 14 which surrounds and supports the lower portion of the blade is provided. It will be appreciated that the closure 8 is only partially threaded, so that the lower portion of the closure 8, which extends from the housing 2, is not threaded.

While in the preferred embodiment of the invention the blade 10 will be presecured to the closure 8, the blade may be provided separately in a compartment in the housing with or without provision for subsequent attachment of the blade to closure 8, if desired.

Disposed within the housing 2, but not illustrated in these figures, are a tracheostomy tube which has a cannula passing therethrough and projecting therebeyond toward the first end of the housing. In a preferred embodiment of the invention, the closure 8 may be secured to the lower end of the housing or, in the alternative, may be secured to the tracheostomy tube which is disposed within the housing. Integrally formed threads or snap-fit engagement, for example, may be employed for this purpose. In use of the invention with the tracheostomy tube and associated cannula, the tracheostomy blade 10 would be used to create an initial opening and the cannula-tracheostomy tube assembly would be passed into the trachea region of the patient through the opening formed by blade 10. The cannula could then be withdrawn from the tube. The tracheostomy tube has a portion adapted to be disposed externally of the patient which may be engaged by the medical practitioner's mouth, an ambu bag or may be connected to other equipment being used to treat the individual. Further details regarding these components and their interrelationship to the assembly illustrated in FIGS. 1 through 7 will be provided hereinafter.

The external thread 16 on closure 8, shown in FIG. 4 could cooperate with internal threads on the lower portion of housing 2 to permit threaded engagement between closure 8 and tubular housing 2. Alternately, the threads on the closure 8 could engage threads on the tracheostomy tube. Also, as a further alternate a snap fit engagement or resilient interfit can be employed. Referring now in greater detail to FIG. 5, there is shown the nasal airway of the present invention with closures 4 and 8 both removed. As will be noted at the lower end of housing 2, internal threads 20 are provided so as to cooperate with external thread 16 of closure 8.

Referring to the upper portion of FIG. 5, it is noted that in this embodiment a writing implement which has a supply of material to be deposited during writing and means for permitting contact between the material and a writing surface are provided. In the form shown the writing implement is a pen having a cone 22 terminating in a pen point 24 through which ink stored in a reservoir (not shown in this view) may be discharged. The lower portion of the cone 22 has external threads which cooperate with internal threads (not shown) of the end of airway tube 26 so as to permit threaded interengagement therebetween. It is also noted that the airway tube 26 has external threads 28 which cooperate with internal threads (not shown in this view) within the upper portion of housing 2 to permit securement of the airway tube to the housing in a storage position.

Referring to FIG. 6 in greater detail there is shown a cross-sectional illustration of the nasal airway of the present invention. It is noted that the housing 2 is provided with an outwardly projecting annular rib 30 over which closure 4 is adapted to be engaged in snap-fit arrangement. In general, the interior surface of closure 4 generally toward the lower extremity thereof would have an inwardly projecting annular rib which would permit the desired snap-fit securement.

As is shown toward the upper portion of FIG. 6, an ink reservoir 32 is operatively associated with pen cone 22 and external threads 34 on pen cone 22 cooperate with internal threads 36 on the nasal airway tube 26. It is also noted that the external threads 28 on airway tube 26 cooperate with internal threads 40 to secure the airway tube 26 to the housing 2.

In the form shown in FIG. 6, the airway tube 26 is in storage position with a major portion of the tube 26 being disposed within tubular housing 2. In this position the lower end opening 44 of airway tube 26 is disposed closer to the lower end 46 of housing 2 than is the upper end 48 of tube 26. The pen reservoir 32 is received within tube 26. While not shown in this view, the blade 10 may be received within the opening or bore of tube 26, may be positioned beside the same or the relative lengths of tube 26 and blade 10 may be such as to create axial spacing along the housing interior therebetween.

In a preferred form, the airway tube 26 will be composed of a resilient material such as a material selected from the group consisting of natural or synthetic rubber, such as latex, for example or plastic. Also, it is preferred that the outer surface of the airway tube 26 either be composed of a somewhat resilient material or that at least a portion of the tube adjacent tube end 44 be covered by a water soluble lubricant such as lanolin, for example. Also, products sold under the trade designation Acid Mantle (buffered aluminum acetate) or the trade designation Aquaphor may be used. This will serve to facilitate insertion of the tube into the nasal passageway of the patient.

Another preferred feature of the invention illustrated in FIG. 6 is the auxiliary opening 50 in tube 26 which is disposed in relative close proximity to tube end 44. In the event that through mucous or other means blockage of the end 44 occurs, functioning of the airway can continue through opening 50 which has its closest portion preferably spaced about ½ inch to 1 inch from end 44. It will be appreciated that a plurality of such openings 50 may be provided, if desired. The positioning and number of openings 50 may be varied as a function of the softness of the material with fewer openings being employed in softer materials.

FIG. 7 shows the airway in the position in which it would appear during usage with the tube 26 projecting outwardly and being threadedly or otherwise secured to housing 2. The end 44 of nasal airway would be inserted into the patient's nostril and the end 46 of tubular housing 2 would be inserted into the mouth of the individual applying resuscitative procedures.

FIG. 8 shows a portion of a preferred construction for tube 26. While the tube 26 may be formed as a unitary article, in the form shown in FIG. 8 it is multipiece. The upper sleeve 27 terminates in an inwardly offset downwardly projecting flange 29. The lower portion of the tube 26 may be secured, as by self-bonding or adhesive means to the radially outer portion of flange 29. This permits the use of different materials for the two portions of tube 26 without engaging in complex molding procedures.

It will be appreciated that while the principal objective of the present invention is to provide readily available, miniaturized resuscitation equipment and this may be accomplished without providing the tracheostomy blade and the writing instrument such as a pen, in the preferred embodiment of the invention the presence of the tracheostomy blade may be advantageous in respect, of numerous emergencies and the pen will not only provide a further function for the apparatus, but also greatly enhance the likelihood that the individual will have the instrument in his or her possession when an emergency occurs. While a blade 10 has been illustrated and disclosed it will be appreciated that other cutting means suitable for creating the desired initial opening may be employed.

Referring to FIGS. 9 through 13, preferred features of the present invention will be considered. It is seen that the housing 2 has the airway tube 26 secured in its storage position in this view. A tracheostomy tube 70 is disposed within the housing. The tube has a first generally cylindrical portion 74 connected to a second generally cylindrical portion 72 by transitional section 78. In the preferred embodiment, the first generally cylindrical portion 74 will be of larger diameter than the second generally cylindrical portion 72 with the preferred ratio of diameters measured internally being about 3:1 to 5:1. It will be appreciated that a bore 76 extends through the smaller diameter portion 72 and is in communication with a counter-bore portion 79 of the large diameter portion 74. It will also be noted that, in the preferred form, the first portion 74 preferably has a greater axial extent than the second portion 72. The ratio of the axial extent of the second portion 72 to that of the first portion 74 is preferably about 0.75:1 to 3:1. In the form illustrated, the cylindrical portion 74 has external threads 75 which cooperate with internal threads 20 of the housing tube to thereby effect a threaded connection. A cannula 90 having a shank portion 91, an end opening 92 and a handle portion 94 is preferably received within the first portion 72 and second portion 74 of the tracheostomy tube 70 and passes through bore 76 preferably projecting therebeyond. The cannula 90 has a handle portion 94 and a tubular bore 96 to thereby permit communication therethrough. The handle 94 of cannula 90 is preferably composed of resilient material so as to be received in snap-fit or resilient engagement within the bore 79 of portion 74. By way of example, large diameter portion 74 may have an external diameter of about 15 mm and small diameter portion 72 may have a diameter of axial extent, for example, of about 1 to 3 inches and the large diameter portion 74 may have an axial extent of about 1½ decisions inches.

Closure 80 has an endwall 82 with a pedestal 84 and a lateral wall 86. A blade member 88 is fixedly secured to the pedestal 84. The external portions of lateral wall 86 are provided with external threads 85 which are threadedly engaged with threads 87 disposed on the lower portions of the inner surface of cannula handle 94. Resilient or snap-fit could be employed if desired. Preferably, the handle 94 of cannula 90 extends further downwardly than first portion 74 in order to facilitate ease of removal of the cannula 90 once closure 80 has been withdrawn. In this manner, when it is desired to gain access to tracheostomy performing apparatus, one need merely open closure 80 to remove blade 88 for use in performing a tracheostomy. Subsequently, the tracheostomy tube 70 and its associated cannula 90 may be withdrawn from the housing. It will be noted that in the form illustrated, the free end 92 of the cannula extends into the hollow portion of airway tube 26.

Assuming that the tracheostomy blade and writing implement are part of the particular embodiment of the invention being carried by an individual, the procedure for operating the same will now be considered. First of all, in the form shown should a tracheostomy be required, the individual need merely remove closure 8 or 80 by unthreading the same from tubular housing 2 and removing the protective covering material 12 from the blade 10 or 88 thereby exposing the blade and permitting closure 8 to function as a handle in using the same. The blade 10 or 88 is employed to provide the desired opening. Subsequently, the tracheostomy tube 70 and its associated cannula 90 which have been removed from the housing 2 are introduced through the opening with the cannula being used to create an opening of the desired size in any portion of the neck region which was not fully opened by the blade 10, 88. After this has been accomplished, the cannula 90 may be withdrawn from the tracheostomy tube 70 and an individual's mouth may be applied to the first portion 74 in order to permit air to be introduced through the apparatus. Alternately, portion 74 25 is so sized as to readily receive an ambu bag or to permit securement to ventilating equipment. Assuming that the airway is to be employed, the pen cone 22 is unthreaded from the airway tube 26 and the airway tube 26 is unthreaded from the tubular housing 2. Subsequently, the airway tube 26 is removed from the housing 2, is reversed and then threadedly connected to the housing at thread 20 thereby permitting insertion of the airway tube 26 into the patient's trachea (or in the event of no tracheostomy, into the nostril) and administration of air or other material through end 46 of housing 2. The sequence in which these two unthreading operations is accomplished is not critical. If desired, the tube 26 could be removed from housing 2 first and subsequently the pen cone 22 removed from tube 26.

Figure 14:
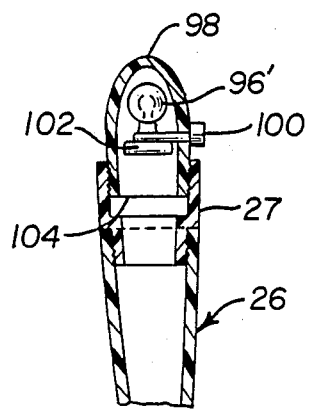
FIG. 14 is a partial cross-sectional illustration of a modified form of the present invention.

Referring to FIG. 14, a further embodiment of the invention will be considered. In this embodiment, the airway 26 and the connection portion 27 are secured to a flashlight. The flashlight has a bulb 96', a transparent dome 98, a switch 100 and a battery 102, all of which is contained within the housing 104 which may be threadedly secured to annular member 27. In this fashion, a useful article of another type may be employed. If desired, a closure (not shown) may be fitted over dome 98 so as to protectively surround the flashlight portion.

It will be appreciated that the housing and associated airway and tracheostomy apparatus may be incorporated in other useful articles apart from pens and flashlights and such other uses will be apparent to those skilled in the art.

It will be appreciated, therefore, that the present invention provides an economical and effective means for starting emergency medical treatment when resuscitation is needed by way of airway or a tracheostomy need be performed. All of this is accomplished while permitting the apparatus to function as a writing implement, flashlight or other useful article thereby providing another dimension of utility and enhancing the likelihood that the instrument will be present during an emergency need.

Whereas particular embodiments of the invention have been described above for purposes of illustration, it will be evident to those skilled in the art that numerous variations of the details may be made without departing from the invention as defined in the appended claims.

I claim:

1. A nasal airway comprising
a tubular housing having a first end and a second end,
a first internal threaded portion at the first end of said tubular housing and a second internal threaded portion at the second end thereof,
an airway tube being of smaller diameter than said housing, said airway tube having a free end insertable into a patient's nostril and an external threaded portion on the opposite end from said free end,
said airway tube when in a storage position having said free end within said tubular housing and said external threaded portion secured to said first internal threaded portion of said tubular housing and when in a use position having said free end external of said tubular housing and said external threaded portion secured to said first internal threaded portion of said tubular housing,
tracheostomy tube means removably secured within said housing generally adjacent to said second end, and
cannula means removably secured within said tracheostomy tube means.

2. The nasal airway of claim 1 including,
first closure means removably covering said tubular housing first end, and
second closure means removably covering said tubular housing second end.

3. The nasal airway of claim 2, including
said tracheostomy tube means having a first tubular portion and second tubular portion,
said first tubular portion having a larger diameter than said second tubular portion thereof, and
said first tubular portion being closer than said second tubular portion to the second end of said housing, said first tubular portion having external threads which cooperative with the second internal threaded portion of said housing and the second tubular portion being within said housing when in a storage position.

4. The nasal airway of claim 3 including,
said cannula means extending completely through said tracheostomy tube means and projecting therebeyond 5. The nasal airway of claim 4 including,
said cannula means extending into the free end of said airway tube.

6. The nasal airway of claim 3 including,
tracheostomy cutting means disposed within said housing.

7. The nasal airway tube of claim 6 including,
said tracheostomy cutting means having blade means.

8. The nasal airway of claim 6 including,
removably protective means secured to said tracheostomy cutting means.

9. The nasal airway of claim 6 including,
said tracheostomy cutting means being secured to said second closure means.

10. The nasal airway of claim 9 including,
said second closure means being removably secured to said cannula means.

11. The nasal airway of claim 9 including,
said first portion of said tracheostomy tube means being adapted for connection to an ambu bag.

12. The nasal airway of claim 11 including
an internal threaded portion on the opposite end of said airway tube, and
writing means having a reservoir of material to be deposited during writing, said writing means extending into said airway tube and being removably secured to said first internal threaded portion of said airway tube, said writing means also having a writing fluid discharge end adapted to be received within said first closure means and connected to said writing means material reservoir to receive said material therefrom, whereby removal of said first closure means, said second closure means, said tracheostomy means, said cannula means, and said writing means from the housing will permit removal of the airway tube from said housing and engagement of the external threaded portion of the airway tube with the first threaded portion of the housing such that the free end of the airway tube is disposed on the exterior of said housing thereby creating a nasal airway.

13. The nasal airway of claim 12 including,
said writing means material reservoir extending into said airway tube when said airway tube is in said storage position.

14. The nasal airway of claim 11 including,
a flashlight having means for threadedly securing to said first internal threaded portion of said housing with at least a portion thereof disposed within said housing and the remaining portion thereof projecting outwardly therefrom.

15. The nasal airway of claim 1 including,
said airway tube having at least one auxiliary opening spaced from the ends of said airway tube.

16. The nasal airway of claim 15 including, said auxiliary opening being disposed closer to said free end of said airway tube than to said externally threaded portion of said airway tube.

17. The nasal airway of claim 16 including,
said auxiliary opening being disposed about ½ to 1 inch from said free end of said airway tube.

18. The nasal airway of claim 15 including,
said airway tube being composed of a resilient material.

19. The nasal airway of claim 18 including,
said airway tube being composed of a material selected from the group consisting of rubber and plastic.

20. The nasal airway of claim 19 including,
lubricant means disposed on at least a portion of the exterior of said airway tube.

21. The nasal airway tube of claim 9 including,
said second closure means being threadedly secured to said cannula means.

* * * * *

UNITED STATES PATENT AND TRADEMARK OFFICE
CERTIFICATE OF CORRECTION

PATENT NO. : 4,893,620

DATED : January 16, 1990

INVENTOR(S) : RAJINDAR K. WADHWA

It is certified that error appears in the above-identified patent and that said Letters Patent is hereby corrected as shown below:

On the Title Page, under "References Cited":
    the "Powers" patent no. should be --1,390,720--;

the "Easton" patent date should be --12/1926--;
    the "Leopoldi" patent no. should be --3,706,106-- and patent date should be --12/1972--;
    the "Gandi et al." patent no. should be --4,300,550--;
    the first reference to "Wadhwa Patent 4,440,161" should be deleted.

Column 1, line 35, "25" should be deleted.

Column 6, line 16, after "diameter of", insert --about 3 to 6 mm. The small diameter portion 72 may have an--.

Column 6, line 18, "decisions" should be deleted.

Column 6, line 58, "25" should be deleted.

Claim 3, column 8, line 4, "cooperative" should be --cooperate--.

Signed and Sealed this

Third Day of September, 1991

Attest:

HARRY F. MANBECK, JR.

Attesting Officer

Commissioner of Patents and Trademarks